(12) United States Patent
Lin et al.

(10) Patent No.: US 12,594,304 B2
(45) Date of Patent: Apr. 7, 2026

(54) METHOD FOR TREATING LIVER CIRRHOSIS BY USING COMPOSITION COMPRISING MESENCHYMAL STEM CELL. EXTRACELLULAR VESICLE PRODUCED BY MESENCHYMAL STEM CELL, AND GROWTH FACTOR

(71) Applicant: GWO XI STEM CELL APPLIED TECHNOLOGY CO., LTD., Hsinchu County (TW)

(72) Inventors: Po-Cheng Lin, Hsinchu County (TW); Pi-Chun Huang, Hsinchu County (TW); Zih-Han Hong, Hsinchu County (TW); Ming-Hsi Chuang, Hsinchu County (TW); Yi-Chun Lin, Hsinchu County (TW); Chia-Hsin Lee, Hsinchu County (TW); Chun-Hung Chen, Hsinchu County (TW); Chao-Liang Chang, Hsinchu County (TW); Kai-Ling Zhang, Hsinchu County (TW)

(73) Assignee: GWO XI STEM CELL APPLIED TECHNOLOGY CO., LTD., Hsinchu County (TW)

( * ) Notice: Subject to any disclaimer, the term of this patent is extended or adjusted under 35 U.S.C. 154(b) by 258 days.

(21) Appl. No.: 18/376,545

(22) Filed: Oct. 4, 2023

(65) Prior Publication Data

US 2024/0115616 A1 Apr. 11, 2024

Related U.S. Application Data

(60) Provisional application No. 63/414,918, filed on Oct. 11, 2022.

(30) Foreign Application Priority Data

Sep. 27, 2023 (TW) ................................. 112137164

(51) Int. Cl.
| | |
|---|---|
| *A61K 35/28* | (2015.01) |
| *A61K 9/00* | (2006.01) |
| *A61K 9/127* | (2006.01) |
| *A61P 1/16* | (2006.01) |
| *C12N 5/0775* | (2010.01) |

(52) U.S. Cl.
CPC ............ *A61K 35/28* (2013.01); *A61K 9/0019* (2013.01); *A61K 9/127* (2013.01); *A61P 1/16* (2018.01); *C12N 5/0667* (2013.01); *C12N 2500/02* (2013.01)

(58) Field of Classification Search
CPC .......... A61K 35/28; A61K 9/0019; A61P 1/16
See application file for complete search history.

(56) References Cited

U.S. PATENT DOCUMENTS

2021/0113625 A1* 4/2021 De Francisco ........ A61K 35/28
2021/0196759 A1* 7/2021 Moseley .............. C07K 14/475

* cited by examiner

*Primary Examiner* — Andrew S Rosenthal

(57) ABSTRACT

The present disclosure provides a method for treating liver cirrhosis by using a composition including mesenchymal stem cells, extracellular vesicles produced by the mesenchymal stem cells, and growth factors. The composition of the present disclosure achieves the effect of treating liver cirrhosis through various efficacy experiments.

15 Claims, No Drawings

METHOD FOR TREATING LIVER CIRRHOSIS BY USING COMPOSITION COMPRISING MESENCHYMAL STEM CELL. EXTRACELLULAR VESICLE PRODUCED BY MESENCHYMAL STEM CELL, AND GROWTH FACTOR

CROSS-REFERENCE TO RELATED APPLICATION

This application claims priorities of Provisional application No. 63/414,918, filed on Oct. 11, 2022, and Taiwan patent application No. 112137164, filed on Sep. 27, 2023, the content of which is incorporated herein in its entirety by reference.

BACKGROUND OF THE INVENTION

1. Field of the Invention

The present invention relates to a method for treating liver cirrhosis by using a composition comprising mesenchymal stem cells, extracellular vesicles produced by the mesenchymal stem cells, and growth factors.

2. The Prior Art

Liver cirrhosis is the main cause of liver-related death. In 2017, more than 13 million people died from liver cirrhosis worldwide, accounting for 2.4% of the total global deaths (1.9% in 1990). The global liver cirrhosis treatment market is estimated to be US $14.8 billion, with a compound rate of 10.9% from 2020 to 2030.

Liver inflammation, liver fibrosis, compensated cirrhosis, decompensated cirrhosis and liver failure or liver cancer are common development processes of liver disease. Common causes of hepatitis or liver cirrhosis are hepatitis B virus, hepatitis C virus, alcoholic and non-alcoholic steatohepatitis, etc. Causes of non-alcoholic steatohepatitis are, such as overweight, diabetes, hyperlipidemia and hypertension. The world has invested a large amount of R&D resources and manpower to develop related drugs and vaccines. Hepatitis B vaccine greatly reduces the number of people suffering from hepatitis B. Hepatitis C drugs are used to treat hepatitis C patients with non-decompensated cirrhosis. However, the results of clinical trials of drugs for decompensated cirrhosis are not as good as expected. It is mentioned in the literature that 58% of patients who received interferon C-free oral new drugs (direct acting antivirals, DAAs) achieved sustained virological responses (SVR), but their Child-Pugh score did not improve. It can be seen that in patients with liver cirrhosis who have been treated or cured, although the inflammatory or pathogenic factors have been eliminated, the damaged areas of the liver have not been completely repaired, and there are no relevant drugs on the market for late-stage compensated cirrhosis and decompensated cirrhosis. Severe liver dysfunction can only require liver transplantation. However, the success rate of liver transplantation is low. Even if the liver transplantation is successful, the survival rate 36 months after receiving the liver transplantation is 79%. After liver transplant surgery, long-term drug treatment is required to prevent rejection and graft-versus-host disease (GvHD). In addition, although the inflammatory or pathogenic factors of patients who have been treated or cured of liver cirrhosis have been eliminated, the damaged areas of the liver have not been repaired, which is a dilemma currently faced by patients with liver disease.

Studies have pointed out that co-culture of stem cells and liver tissue can induce the differentiation of stem cells into liver-like cells and promote the recovery of damaged liver. However, this technology requires co-culture of two types of cells and tissues, which is cumbersome and difficult to commercialize. To address the above issues, there is still a need for a new cell-based composition that is clinically safe and therapeutically effective for the treatment of liver cirrhosis.

At present, clinical drug treatments for liver cirrhosis have limited effect and have serious side effects, and many patients cannot continue to treat. More importantly, the drug only alleviates the symptoms, but fails to fundamentally solve the problem, so how to develop a new drug that can effectively treat arthritis is an important issue that the present invention intends to solve here.

In order to solve the above-mentioned problems, those skilled in the art urgently need to develop a novel medicament for treating liver cirrhosis for the benefit of a large group of people in need thereof.

SUMMARY OF THE INVENTION

A primary objective of the present invention is to provide a method for treating liver cirrhosis, comprising administering to a subject in need thereof a medicament comprising an effective amount of a composition comprising a mesenchymal stem cell (MSC), an extracellular vesicle (EV) produced by the mesenchymal stem cell, and a growth factor.

According to an embodiment of the present invention, the mesenchymal stem cell is human adipose-derived mesenchymal stem cell (ADSC).

According to an embodiment of the present invention, the liver cirrhosis is caused by alcoholic liver disease.

According to an embodiment of the present invention, the growth factor is uteroglobin.

According to an embodiment of the present invention, the growth factor is selected from the group consisting of: granulocyte colony-stimulating factor (G-CSF), granulocyte-macrophage colony-stimulating factor (GM-CSF), hepatocyte growth factor (HGF), insulin-like growth factor binding proteins-4 (IGFBP-4), insulin-like growth factor binding proteins-6 (IGFBP-6), interleukin-2 (IL-2), platelet-derived growth factor-AB/BB (PDGF-AB/BB), transforming growth factor-$\alpha$ (TGF$\alpha$), vascular endothelial growth factor (VEGF-A), IL-18 binding protein-$\alpha$ (IL-18BP$\alpha$), angiopoietin-like 3 (ANGPTL-3), fibroblast growth factor-19 (FGF-19), matrix metalloproteinase-2 (MMP-2), MMP-3, MMP-7, MMP-9, MMP-10, MMP-12, and a combination thereof.

According to an embodiment of the present invention, the growth factor is IL-2, PDGF-AB/BB or TGF$\alpha$, and expressions of the IL-2, PDGF-AB/BB and the TGF$\alpha$ are down-regulated.

According to an embodiment of the present invention, the mesenchymal stem cell has an effective concentration of liver injection of $7\times10^7$-$1\times10^8$ mesenchymal stem cells.

According to an embodiment of the present invention, the composition increases expressions of interleukin-10 (IL-10) and interferon gamma (INF-$\gamma$).

According to an embodiment of the present invention, the composition reduces levels of aspartate aminotransferase (AST) and alanine aminotransferase (ALT).

According to an embodiment of the present invention, the composition has ability to repair liver damage and improves regeneration ability of damaged liver.

According to an embodiment of the present invention, the composition enhances synthesis ability of albumin, metabolism ability of bilirubin, synthesis ability of prothrombin, and synthesis and metabolism ability of liver.

According to an embodiment of the present invention, the human ADSC is expanded by using the keratinocyte serum-free medium (SFM) supplemented with 1-100 mM N-acetyl-L-cysteine and 0.05-50 mM L-ascorbic acid 2-phosphate.

According to an embodiment of the present invention, the human ADSC is further expanded in a culture flask made of a material with an oxygen-containing functional group at ratio of 20-35%.

According to an embodiment of the present invention, therapeutic effect of the liver cirrhosis lasts for at least 6 months.

According to an embodiment of the present invention, the medicament is in a dosage form for parenteral administration.

Another objective of the present invention is to provide a medicament for treating liver cirrhosis, comprising a mesenchymal stem cell (MSC), an extracellular vesicle (EV) produced by the mesenchymal stem cell, and a growth factor.

In summary, the composition comprising the mesenchymal stem cell (MSC), the extracellular vesicle (EV) produced by the mesenchymal stem cell, and the growth factor of the present invention has the following effect. Via liver injection, a suspension comprises at least stem cells, active synergistic ingredients, and growth factors, in which CD73 can be can highly expressed on stem cells, and the pharmaceutical composition can reduce aspartate aminotransferase (AST or GOT) and alanine aminotransferase (ALT or GPT) by highly expressing IL-10 and INF-γ. The pharmaceutical composition repairs liver damage and improves regeneration ability of damaged liver, and also enhances synthesis ability of albumin, metabolism ability of bilirubin, synthesis ability of prothrombin, and synthesis and metabolism ability of liver for more than half a year.

DETAILED DESCRIPTION OF THE PREFERRED EMBODIMENT

In the following detailed description of the embodiments of the present invention, reference is made to the accompanying drawings, which are shown to illustrate the specific embodiments in which the present disclosure may be practiced. These embodiments are provided to enable those skilled in the art to practice the present disclosure. It is understood that other embodiments may be used and that changes can be made to the embodiments without departing from the scope of the present invention. The following description is therefore not to be considered as limiting the scope of the present invention.

Definition

As used herein, the data provided represent experimental values that can vary within a range of ±20%, preferably within ±10%, and most preferably within ±5%.

Unless otherwise stated in the context, "a", "the" and similar terms used in the specification (especially in the following claims) should be understood as including singular and plural forms.

According to the present invention, the term "adipose-derived stem cells (ADSCs)" refers to mesemchymal stem cells separated from fat, which are multipotent stem cells having high plasticity. After induction, they can be differentiated into cells of many different tissues.

According to the present invention, the extracellular vesicle comprises exosome and microvesicles.

As used herein, the term "treating" or "treatment" refers to alleviating, reducing, ameliorating, relieving, or controlling one or more clinical signs of a disease or disorder, and lowering, stopping, or reversing the progression of severity regarding the condition or symptom being treated.

According to the present invention, the medicament can be manufactured to a dosage form suitable for parenteral administration, using techniques well known to those skilled in the art, including, but not limited to, injection (e.g., sterile aqueous solution or dispersion), sterile powder, tablet, troche, lozenge, pill, capsule, dispersible powder or granule, solution, suspension, emulsion, syrup, elixir, slurry, and the like.

The medicament according to the present invention may be administered by a parenteral route selected from the group consisting of: intraperitoneal injection, subcutaneous injection, intraepidermal injection, intradermal injection, intramuscular injection, intravenous injection, and intralesional injection.

The medicament according to the present invention can comprise a pharmaceutically acceptable carrier which is widely used in pharmaceutical manufacturing technology. For example, the pharmaceutically acceptable carrier can comprise one or more reagents selected from the group consisting of solvent, emulsifier, suspending agent, decomposer, binding agent, excipient, stabilizing agent, chelating agent, diluent, gelling agent, preservative, lubricant, absorption delaying agent, liposome, and the like. The selection and quantity of these reagents fall within the scope of the professional literacy and routine techniques of those skilled in the art.

According to the present invention, the pharmaceutically acceptable carrier comprises a solvent selected from the group consisting of water, normal saline, phosphate buffered saline (PBS), sugar solution, aqueous solution containing alcohol, and combinations thereof.

Examples 1-4

According to the present invention, the cells used in the following examples are human adipose-derived mesenchymal stem cells (ADSCs).

According to the present invention, liposuction was performed from healthy donors during abdominal surgery. 2-5 g of adipose tissue was collected from the subcutaneous fat of the abdominal wall. The liposuction operation takes about 1 hour and the wound is less than 1 cm. All donors provide informed consent form (ICF). Human adipose tissue was placed in $Ca^{2+}/Mg^{2+}$-free phosphate buffered saline (PBS) and immediately transferred to the laboratory.

According to the present invention, human adipose tissue was removed from shipping medium and placed in a Petri dish. The adipose tissue was washed 3 to 4 times using $Ca^{2+}/Mg^{2+}$-free phosphate buffered saline (PBS) and cut into small pieces (volume approximately 1-3 mm 3). The tissue was dissociated with 0.1-0.3% collagenase in a temperature environment of 36.5-38.5° C. for 60 minutes. After collagenase digestion, centrifugation was performed at 20-25° C. and 500 g for 5-15 minutes to separate cells and undigested tissue fragments from stromal vascular fraction (SVF) pellets. The dissociated cells were collected and cultured at 36.5-38.5° C. in an incubator providing 5% $CO_2$. After 1 to 2 days of culture, the supernatant and debris were removed from the culture to obtain primary adipose-derived mesenchymal stem cells.

The primary adipose-derived mesenchymal stem cells were then expanded and cultured in different culture media. The culture media used in each example are as follows.

Example 1: $0.5\times10^5$ adipose-derived mesenchymal stem cells were placed in a 6-well cell culture plate (Corning) comprising 1-100 mM N-acetyl-L-cysteine (Sigma), 0.05-50 mM L-ascorbic acid 2-phosphate (Sigma) in keratino-cyte-serum free medium (SFM) (Gibco) for cell culture for 1, 4, and 7 days. The culture environment is a cell culture incubator with a temperature controlled at 36.5-38.5° C. and containing 5% carbon dioxide.

Example 2: $0.5\times10^5$ adipose-derived mesenchymal stem cells were placed in a 6-well cell culture plate (Corning) comprising 1-10 mg/ml human serum albumin (Bio-Pure), 0.05-50 mM L-ascorbic acid 2-phosphate, and 1-40 mM sodium bicarbonate (Sigma) in DMEM/F12 medium (Gibco) for cell culture for 1, 4, and 7 days. The culture environment is a cell culture incubator with a temperature controlled at 36.5-38.5° C. and containing 5% carbon dioxide.

Example 3: $0.5\times10^5$ adipose-derived mesenchymal stem cells were placed in a 6-well cell culture plate (Corning) comprising 1-10 mg/ml human serum albumin (Bio-Pure), 0.05-50 mM L-ascorbic acid 2-phosphate, 1-40 mM sodium bicarbonate (Sigma), and 5-15 mM HEPES (Sigma) in DMEM/F12 medium (Gibco) for cell culture for 1, 4, and 7 days. The culture environment is a cell culture incubator with a temperature controlled at 36.5-38.5° C. and containing 5% carbon dioxide.

Example 4: $0.5\times10^5$ adipose-derived mesenchymal stem cells were placed in a 6-well cell culture plate (Corning) comprising 5-20 wt % fetal bovine serum (Hyclone) in DMEM/F12 medium (Gibco) for cell culture for 1, 4, and 7 days. The culture environment is a cell culture incubator with a temperature controlled at 36.5-38.5° C. and containing 5% carbon dioxide.

Cell survival rate was assessed with ADAM-MC™ Automatic Cell Counter (Digital Bio, NanoEnTek Inc.). When the culture days were 1, 4, and 7 days, cell activity and the number of cells in each example were analyzed, and the results were recorded in Table 1.

TABLE 1

|  |  | Example 1 | Example 2 | Example 3 | Example 4 |
|---|---|---|---|---|---|
| Number of cells | Day 1 | 0.457 × $10^5$ | 0.369 × $10^5$ | 0.432 × $10^5$ | 0.336 × $10^5$ |
|  | Day 4 | 5.534 × $10^5$ | 3.460 × $10^5$ | 4.174 × $10^5$ | 1.548 × $10^5$ |
|  | Day 7 | 8.765 × $10^5$ | 6.808 × $10^5$ | 7.904 × $10^5$ | 1.860 × $10^5$ |

As shown in the results in Table 1, whether it is the 4th day or the 7th day, the number of cells in Example 1 is the highest, followed by Example 3, Example 2, and Example 4 in sequence. The number of cells in Example 4 is significantly less than that of the other three groups.

In addition, cluster of differentiation (CD) refers to cell surface markers that cells of different lineages express or disappear during different stages of normal differentiation and maturation and activation processes. The CD marker is a protein complex or glycoprotein on the cell membrane. CD markers have many uses and are often used as important receptors or ligands of cells. At the same time, they can be used as a surface marker for cell identification and isolation, and are widely involved in various stages of cells, including cell growth, cell differentiation, cell migration, etc. CD29 (integrin (31) is a multi-functional protein involved in cell-matrix adhesion, cell signaling, cellular defense, cell adhesion, protein binding, protein heterodimerization, receptor-mediated activity, wound repair, etc. CD44 (hy-aluronate) is expressed on stem cells and cells in the niches surrounding, including inflammatory cells. CD73 (5'ecto-nucleotidase) is a ubiquitously expressed glycosylphospha-tidylinositol-anchored glycoprotein (GPI) and a regulator of immune function. It can reduce alcohol-induced liver dam-age and inflammation by blocking the TLR4/MyD88/NF-κB signaling pathway, thereby improving liver damage. CD90 (Thy-1) plays a key role in adipose-derived mesenchymal stem cell proliferation and metabolism by activating AKT and cyclin D1. CD105 (endoglin) can be relatively specific markers of adipose-derived mesenchymal stem cells. Stud-ies have shown that adipose-derived mesenchymal stem cells (CD105⁺ADSCs) expressing CD105 have a higher growth rate and differentiation ability. Therefore, on the 7th day of culture, the surface antigen expression levels of the adipose-derived mesenchymal stem cells obtained in Examples 1 to 3 were analyzed respectively. 100 µL of $1\times10^6$ cells/mL adipose-derived mesenchymal stem cells were taken into a microcentrifuge tube, and fluorescently labeled CD73, CD90, CD105, CD14, CD19, CD34, CD45, HLA-DR (Becton Dickinson) antibodies were added at a ratio of 1:100 and mixed evenly. After standing in the dark, cell markers were analyzed using a BD AccuriC6 flow cytometer (Becton Dickinson). After the analysis was com-pleted, the results were recorded in Table 2.

TABLE 2

|  |  | Example 1 | Example 2 | Example 3 |
|---|---|---|---|---|
| Surface antigen expression level (%) | CD 73 | 99.96 | 99.81 | 99.66 |
|  | CD 90 | 100 | 99.98 | 99.94 |
|  | CD 105 | 99.19 | 99.69 | 98.17 |
|  | CD 14 | 0.06 | 0.07 | 0.15 |
|  | CD 19 | 0.06 | 0.17 | 0.13 |
|  | CD 34 | 0.07 | 0.29 | 0.23 |
|  | CD 45 | 0.10 | 0.16 | 0.18 |
|  | HLA-DR | 0.04 | 0.07 | 0.12 |

Surface antigens in each example were confirmed. High levels of specific mesenchymal stem cell markers CD73, CD90 and CD105 were expressed on the ADSCs cultured in Examples 1 to 3. The molecular expression levels of hema-topoietic cell markers CD14, CD19, CD34, CD45 and HLA-DR were very low, consistent with the characteristics of adipose-derived mesenchymal stem cells.

In addition, the doubling-time of the cells after the sev-enth day of culture in Examples 1 to 4 was compared, and the results obtained are as shown in Table 3.

TABLE 3

|  | Example 1 | Example 2 | Example 3 | Example 4 |
|---|---|---|---|---|
| doubling-time (hour) | 20.01 | 22.30 | 22.00 | 32.67 |
| doubling-time (Take Example 4 as 100%) | 38.8% shorter | 31.7% shorter | 32.7% shorter | — |

The doubling time of Example 1 is 20.01 hours, and the doubling times of Examples 2 to 4 are 22.30 hours, 22.00 hours and 32.67 hours respectively.

From the above results, it can be seen that the culture medium used in Example 1 can more effectively increase the expansion number of adipose-derived mesenchymal stem cells than the culture medium used in other examples, and would not affect cell activity and surface antigen characteristics.

Examples 5 and 6

In this embodiment, the primary adipose-derived mesenchymal stem cells obtained in the same manner as in the aforementioned Examples 1 to 4 were placed in a culture flask made of a material with an oxygen-containing functional group at ratio of 20-35% and an oxygen-containing functional group at ratio of 5-20% material culture flasks for cell expansion. The outer material of the culture flask whose oxygen-containing functional group ratio is 20-35% is polystyrene. Due to the incorporation of oxygen-containing functional groups on the polystyrene surface, the culture surface has a net negative surface charge, making the surface of the culture flask more hydrophilic and moist, which helps cell attachment and growth. The culture methods of each embodiment are as follows.

Example 5: $1\times10^6$ adipose-derived mesenchymal stem cells were cultured in a culture flask (HYPERFlask, Corning) with an oxygen-containing functional group at ratio of 20-35% using the same culture medium components as Example 1 for 14 days. The culture environment is a cell culture incubator with a temperature controlled at 36.5-38.5° C. and containing 5% carbon dioxide.

Example 6: $1\times10^6$ adipose-derived mesenchymal stem cells were cultured in a culture flask (175T Flask, Corning) with an oxygen-containing functional group at ratio of 5-20% using the same culture medium components as Example 1 for 14 days. The culture environment is a cell culture incubator with a temperature controlled at 36.5-38.5° C. and containing 5% carbon dioxide.

When culturing for 10 to 14 days, the cell number, cell survival rate, and surface antigen expression level of Examples 5 and 6 were analyzed respectively, and the results were recorded in Table 4.

TABLE 4

| | | Example 5 | Example 6 |
|---|---|---|---|
| The number of cells obtained per cm$^2$ | | 49,612 | 31,761 |
| cell survival rate | | 95% | 96% |
| surface antigen | CD 29 | 99.99 | 99.95 |
| expression level (%) | CD44 | 99.96 | 99.96 |
| | CD 90 | 100 | 99.98 |
| | CD 105 | 97.82 | 97.13 |
| | CD 14 | 0.00 | 0.02 |
| | CD 34 | 0.03 | 0.01 |
| | CD 45 | 0.02 | 0.03 |
| | HLA-DR | 0.13 | 0.15 |

From the results in Table 4 above, it can be seen that the number of cells in Example 5 increased from $1\times10^6$ cells to $2.56\times10^8$ cells (49,612 cells/cm 2). The number of cells in Example 6 ranged from $1\times10^6$ cells to $1.64\times10^8$ cells (31,761 cells/cm$^2$). It can be seen that under the same culture medium components, when adipose-derived mesenchymal stem cells were cultured in a culture flask made of a material with an oxygen-containing functional groups at ratio of 20-35%, the expansion speed would be significantly faster than that of a culture flask cultured with an oxygen-containing functional group at ratio of 5-20%.

Further, the surface antigens of each example were confirmed. High levels of specific mesenchymal stem cell markers CD90 and CD105 were expressed on the ADSCs cultured in Examples 5 and 6. The expression levels of hematopoietic cell markers CD14, CD34, CD45 and HLA-DR molecules were very low, consistent with the characteristics of adipose-derived mesenchymal stem cells.

From the above results, it can be seen that the culture flask used in Example 5 can more effectively increase the expansion number of adipose-derived mesenchymal stem cells than the culture flask used in Example 6, and would not affect cell activity and surface antigen characteristics.

Example 7 and Comparative Example 1

In this embodiment, the primary adipose-derived mesenchymal stem cells obtained in the same manner as in the aforementioned Examples 1 and 3 are used for cell expansion. The culture method in each example is as follows.

Example 7: $1\times10^7$ adipose-derived mesenchymal stem cells were cultured in a culture flask with an oxygen-containing functional group at ratio of 20-35% using the same culture medium components as Example 1 for 7 days. The culture environment is a cell culture incubator with a temperature controlled at 36.5-38.5° C. and containing 5% carbon dioxide.

Comparative Example 1: $1\times10^7$ adipose-derived mesenchymal stem cells were cultured in a culture flask with an oxygen-containing functional group at ratio of 20-35% using the same culture medium components as Example 3 for 7 days. The culture environment is a cell culture incubator with a temperature controlled at 36.5-38.5° C. and containing 5% carbon dioxide.

When cultured to the 7th day, the cell numbers of each embodiment were analyzed respectively. As a result, it was found that the number of cells in Example 7 increased from $1\times10^7$ cells to $7.88\times10^7$ cells, while the number of cells in Comparative Example 1 decreased from $1\times10^7$ cells to $1.96\times10^6$ cells. It can be seen from this result that not all culture media and culture flasks made of materials with an oxygen-containing functional group at ratio of 20-35% can expand the number of adipose-derived mesenchymal stem cells. The number of adipose-derived mesenchymal stem cells can be most efficiently expanded by using the culture medium of Example 1 and a culture flask made of a material with an oxygen-containing functional group at ratio of 20-35% (Example 7).

Example 8

Extracellular Vesicle Analysis

Extracellular vesicles (EVs) are heterogeneous particles formed by outward budding or exocytosis of original cells. They have no functional nuclei and cannot be replicated. Extracellular vesicles include exosomes and microvesicles. The extracellular vesicle has diameter ranging from 30 nm to 1 μm. Extracellular vesicles are cell-derived particles wrapped in a lipid bilayer membrane and contain proteins, lipids, nucleic acids, etc. Extracellular vesicles are usually rich in tetraspanin proteins on the cell surface, mainly CD9, CD63, CD81 and other proteins, such as ALG-2 interacting protein-X (Alix) and tumor susceptibility gene 101 (TSG101). Alix, also known as programmed cell death 6 interacting protein (PDCD6IP), is an adapter protein that binds to ESCRT and endophilin-A protein. TSG101 and signal-transducing adapter molecules play key roles in exosome biogenesis and secretion, thereby enhancing exosome secretion.

$1\times10^8$ adipose-derived mesenchymal stem cells expanded and cultured for 14 days in Example 7 were mixed with saline, and left to stand in an environment of 2 to 10° C. for 1, 2, 4, 8, 16, 24, 36, and 48 hours, followed by analyzing extracellular vesicles in the liquid.

Following the above, the supernatant was taken out and moved to a new tube, and then centrifugation was performed at an acceleration of 4000 g for 20 minutes. The supernatant was removed and filtered through a 0.22 μm filter (Merck Millipore, Billerica, MA, USA) to remove large vesicles. Amicon Ultra-15 with a molecular weight exceeding 100 kDa (Millipore) was used to remove free proteins, and then the supernatant containing extracellular vesicles was obtained by centrifugation at an acceleration of 4000 g. The concentration and particle size of extracellular vesicles in the solution were analyzed, and the results were recorded in Table 5.

TABLE 5

| Resting time (hours) | Number of cells | Saline (ml) | Extracellular vesicle | | |
|---|---|---|---|---|---|
| | | | Particle size (nm) | Concentration (particle/ml) | Concentration (particle/cell) |
| 1 | $1 \times 10^8$ | 1 | 77.3 ± 1.3 | $1.17 \times 10^{12}$ | $9.59 \times 10^3$ |
| 2 | $1 \times 10^8$ | 1 | 76.2 ± 1.3 | $9.53 \times 10^{11}$ | $1.33 \times 10^4$ |
| 4 | $1 \times 10^8$ | 1 | 91.5 ± 1.7 | $7.62 \times 10^{11}$ | $9.92 \times 10^3$ |
| 8 | $1 \times 10^8$ | 1 | 89.7 ± 0.5 | $1.63 \times 10^{12}$ | $1.58 \times 10^4$ |
| 16 | $1 \times 10^8$ | 1 | 148.3 ± 1.2 | $4.37 \times 10^{12}$ | $5.95 \times 10^4$ |
| 24 | $1 \times 10^8$ | 1 | 75.7 ± 0.6 | $1.25 \times 10^{13}$ | $1.46 \times 10^5$ |
| 36 | $1 \times 10^8$ | 1 | 82.9 ± 0.6 | $7.29 \times 10^{12}$ | $1.05 \times 10^5$ |
| 48 | $1 \times 10^8$ | 1 | 98.7 ± 0.3 | $6.08 \times 10^{12}$ | $6.79 \times 10^4$ |

As shown in Table 5, $1\times10^8$ adipose-derived mesenchymal stem cells expanded and cultured for 14 days in Example 7 were mixed with saline. After standing in an environment of 2-10° C. for 1, 2, 4, 8, 16, 24, 36, and 48 hours, the concentration of extracellular vesicles reached the highest when the standing time was 24 hours. Afterwards, the concentration of extracellular vesicles decreased with prolonged standing time.

In addition, the adipose-derived mesenchymal stem cells expanded and cultured for 14 days in Example 7 were mixed with phosphate buffered saline (DPBS) or saline in the ratios shown in Table 6, standing for 24 hours at 2-10° C., followed by centrifugation at 300 g for 5 minutes. The supernatant was removed and transferred to a new tube. Centrifugation was performed at 4000 g for 20 minutes, and then the supernatant was filtered through a 0.22 nm filter (Merck Millipore, Billerica, MA, USA) to remove large vesicles. Amicon Ultra-15 with a molecular weight exceeding 100 kDa (Millipore) was used to remove free proteins, and then the supernatant containing extracellular vesicles was obtained by centrifugation at an acceleration of 4000 g. The concentration and particle size of extracellular vesicles in the solution were analyzed, and the results were recorded in Table 6.

TABLE 6

| | Number of cells | DPBS (ml) | Saline (ml) | Extracellular vesicle | | |
|---|---|---|---|---|---|---|
| | | | | Particle size (nm) | Concentration (particle/ml) | Concentration (particle/cell) |
| First group | $7 \times 10^7$ | 1 | 0 | 80.9 ± 0.6 | $8.595 \times 10^{12}$ | $1.23 \times 10^5$ |
| Second group | $7 \times 10^7$ | 1 | 0 | 92.7 ± 1.9 | $8.73 \times 10^{12}$ | $1.25 \times 10^5$ |
| Third group | $1 \times 10^8$ | 0 | 1 | 84.4 ± 0.5 | $1.20 \times 10^{13}$ | $1.20 \times 10^5$ |
| Fourth group | $1 \times 10^8$ | 0 | 1 | 89.0 ± 0.7 | $1.16 \times 10^{13}$ | $1.16 \times 10^5$ |

As shown in Table 6, $7\times10^7$ or $1\times10^8$ adipose-derived mesenchymal stem cells expanded and cultured for 14 days in Example 7 were mixed with phosphate buffered saline (DPBS) or saline. After standing in an environment of 2-10° C. for 24 hours, extracellular vesicles were analyzed. The results showed that the adipose-derived mesenchymal stem cells expanded after 14 days of culture in Example 7, whether in PBS or saline, $7\times10^7$ or $1\times10^8$ adipose-derived mesenchymal stem cells, the concentration of extracellular vesicles produced by which is above $1.23\times10^5$ particles/cell.

The adipose-derived mesenchymal stem cell culture medium solution expanded in Example 7 and the culture medium solution of Example 1 were subjected to RayBiotech human growth factor antibody array analysis. GE fluorescent luminescence gel instrument and ImageQuan LAS4000 software were used to capture the luminescence image on the array membrane to count the expression of growth factors.

EXPERIMENTAL RESULTS

Taking the control group (culture medium solution in Example 1) as 1, the expression levels of the growth factors of the present invention including granulocyte-colony stimulating factor (G-CSF), granulocyte-macrophage colony-stimulating factor (GM-CSF), hepatocyte growth factor (HGF), insulin-like growth factor binding proteins-4 (IGFBP-4), and insulin-like growth factor binding proteins-6 (IGFBP-6) are shown in Table 7 below.

TABLE 7

| Growth factor | G-CSF | GM-CSF | HGF | IGFBP-4 | IGFBP-6 |
|---|---|---|---|---|---|
| fold | 1.65 | 5.10 | 42.93 | 5.77 | 19.97 |

As shown above, the expressions of G-CSF, GM-CSF, HGF, IGFBP-4 and IGFBP-6 increased in the adipose-derived mesenchymal stem cell culture medium solution expanded in Example 7. It can be seen that the adipose-derived mesenchymal stem cell culture medium solution expanded in Example 7 would produce a large amount of growth factors that have the potential to treat liver cirrhosis, thereby improving liver cirrhosis.

$1\times10^8$ adipose-derived mesenchymal stem cells expanded and cultured for 14 days in Example 7 were mixed with saline, and let stand for 0 to 48 hours in an environment of 2-10° C. Afterwards, centrifugation was performed at 300×g for 5 minutes to collect the supernatant and the extracellular vesicles (EVs) in the supernatant. The supernatant containing EVs was reacted with Exo-Quick-TC (System Biosciences, Palo Alto, CA, USA) at 4° C. for at least 12 hours, and then EVs were precipitated. After completing the precipitation of EVs, treated with protein lysis buffer to obtain protein of EVs. The supernatant and protein of EVs were analyzed for granulocyte colony-stimulating factor (G-CSF), interleukin-2 (IL-2), platelet-derived growth factor-AB/BB (PDGF-AB/BB), transforming growth factor-α (TGFα), vascular endothelial growth factor (VEGF-A), uteroglobin, IL-18 binding protein-α (IL-18BPα), a-fetoprotein (AFP), angiopoietin-like 3 (ANGPTL-3), fatty acid-binding protein-1 (FABP1), fibroblast growth factor-19 (FGF-19), FGF-21, FGF-23, matrix metalloproteinase-2 (MMP-2), MMP-3, MMP-7, MMP-9, MMP-10, MMP-12, and hepatocyte growth factor (HGF) content using MIL-LIPLEX® MAP MULIPLEX DETECTION (Merck Milliplex, instrument model: Luminex Magpix analyzer). The values are recorded in Table 8 (2-10° C.).

growth factors produced during a specific resting time is the composition of the present invention and can be used to treat liver cirrhosis.

In addition, adipose-derived mesenchymal stem cells can also be placed in other injection water until they produce extracellular vesicles and growth factors. For example, it can be selected from distilled water for injection, 0.45-3% sodium chloride injection, 2.5-50% glucose injection, Lactated Ringer's B injection, or Ringer's Solution, no limitation is imposed here.

Example 10

This example is conducted in accordance with the ethical principles of the Declaration of Helsinki and local laws and

TABLE 8

| Factor | Example 7 | | | | | |
| | 0 hr | | 24 hrs | | 48 hrs | |
| (pg/ml) | Supernatant | EVs | Supernatant | EVs | Supernatant | EVs |
|---|---|---|---|---|---|---|
| G-CSF | 2.54 ± 0.53 | 3.34 ± 0.81 | 170.64 ± 6.22 | 50.74 ± 2.26 | 275.16 ± 0.00 | 31.81 ± 4.51 |
| IL-2 | 0.41 ± 0.03 | 0.38 ± 0.03 | 0.27 ± 0.02 | 0.34 ± 0.02 | 0.24 ± 0.02 | 0.30 ± 0.03 |
| PDGF-AB/BB | 4.26 ± 1.48 | 7.68 ± 3.24 | 0.29 ± 0.06 | 1.68 ± 0.32 | 0.08 ± 0.0.02 | 0.09 ± 0.00 |
| TGFα | 0.93 ± 0.07 | 1.04 ± 0.11 | 0.64 ± 0.00 | 060 ± 0.06 | 0.53 ± 0.05 | 0.56 ± 0.00 |
| VEGF-A | 1.60 ± 0.08 | 1.50 ± 0.08 | 73.55 ± 3.92 | 191.12 ± 3.40 | 60.11 ± 1.07 | 220.84 ± 1.96 |
| Uteroglobin | 2.42 ± 0.00 | 2.56 ± 0.06 | 2.77 ± 0.00 | 3.32 ± 0.26 | 2.60 ± 0.25 | 3.32 ± 0.26 |
| IL-18BPα | 1.42 ± 0.00 | 0.99 ± 0.38 | 1.74 ± 0.45 | 2.06 ± 0.00 | 1.74 ± 0.45 | 2.06 ± 0.00 |
| AFP | 0.01 ± 0.00 | 0.01 ± 0.00 | 0.01 ± 0.00 | 0.01 ± 0.00 | 0.01 ± 0.00 | 0.01 ± 0.00 |
| ANGPTL3 | 0.34 ± 0.01 | 0.34 ± 0.01 | 0.29 ± 0.00 | 0.39 ± 0.03 | 0.28 ± 0.01 | 0.38 ± 0.01 |
| FABP1 | 0.02 ± 0.00 | 0.02 ± 0.00 | 0.02 ± 0.00 | 0.02 ± 0.00 | 0.02 ± 0.00 | 0.02 ± 0.00 |
| FGF-19 | 0.05 ± 0.00 | 0.07 ± 0.02 | 0.06 ± 0.00 | 0.12 ± 0.00 | 0.06 ± 0.00 | 0.09 ± 0.00 |
| FGF-21 | 0.00 ± 0.00 | 0.00 ± 0.00 | 0.00 ± 0.00 | 0.00 ± 0.00 | 0.00 ± 0.00 | 0.00 ± 0.00 |
| FGF-23 | 0.01 ± 0.00 | 0.01 ± 0.00 | 0.01 ± 0.00 | 0.01 ± 0.00 | 0.01 ± 0.00 | 0.01 ± 0.00 |
| MMP-1 | 2.90 ± 0.00 | 8.91 ± 5.38 | 1,888 ± 22.63 | 162.15 ± 1.97 | 7,856 ± 211.42 | 303.44 ± 7.37 |
| MMP-2 | 83.56 ± 0.00 | 98.75 ± 13.59 | 1,117 ± 67.88 | 469.03 ± 0.00 | 4,185 ± 50.91 | 786.83 ± 76.29 |
| MMP-3 | 60.73 ± 0.00 | 87.69 ± 24.11 | 195.61 ± 0.00 | 81.21 ± 0.00 | 870.65 ± 46.65 | 92.38 ± 0.00 |
| MMP-7 | 188.80 ± 0.00 | 160.71 ± 25.13 | 239.35 ± 0.00 | 323.18 ± 41.31 | 266.66 ± 38.62 | 383.42 ± 43.88 |
| MMP-9 | 3.28 ± 0.44 | 4.38 ± 1.03 | 251.72 ± 3.05 | 186.40 ± 0.00 | 351.83 ± 8.54 | 265.02 ± 3.21 |
| MMP-10 | 6.52 ± 0.00 | 6.68 ± 0.14 | 6.52 ± 0.00 | 16.35 ± 1.65 | 6.52 ± 0.00 | 21.76 ± 0.88 |
| MMP-12 | 1.00 ± 0.00 | 1.00 ± 0.00 | 1.43 ± 0.13 | 1.36 ± 0.00 | 2.94 ± 0.13 | 2.37 ± 0.13 |
| HGF | 0.01 ± 0.00 | 0.01 ± 0.00 | 0.60 ± 0.01 | 2.07 ± 0.03 | 1.21 ± 0.04 | 3.84 ± 0.04 |

As shown in Table 8, $1×10^8$ adipose-derived mesenchymal stem cells were obtained by culture and expansion in Example 7 for 14 days. After standing for 24 hours in an environment of 2-10° C., the expressions of G-CSF, VEGF-A, uteroglobin, IL-18BPα, MMP-1, MMP-2, MMP-3, MMP-7, MMP-9, MMP-10, MMP-12, and HGF in the supernatant and EVs increased, better than standing in an environment of 37° C. for 24 hours and standing in an environment of 2-10° C. for 48 hours. From the above, after 14 days of culture and expansion in Example 7, the adipose-derived mesenchymal stem cells were left to stand for 24 hours in an environment of 2 to 10° C., and produced a large amount of growth factors that have the potential to treat liver cirrhosis, thereby improving liver cirrhosis.

Example 9

Composition of Present Invention

The adipose-derived mesenchymal stem cells obtained by culture and expansion in Example 7 for 14 days were mixed with phosphate buffered saline (DPBS) or saline, followed by standing for 24 hours in an environment of 2-10° C. As mentioned above, a preparation composed of adipose-derived mesenchymal stem cells, extracellular vesicles and regulations. This example follows the current Good Clinical Trial Practice Guidelines for Drugs.

Subjects must meet the inclusion and exclusion conditions at the same time before they can enter the trial.

The subject selection conditions are integrated as follows.

Inclusion Conditions:

1. Adults with liver cirrhosis aged 20 to 80 years old (inclusive).
2. Liver cirrhosis confirmed by CT angiography, regardless of cause.
3. MELD score 10 to 20 (inclusive) and Child-Pugh B (score 7 to 9). [Note: MELD=model for end-stage liver disease]
4. Provide signed and dated subject consent form.

Exclusion Conditions:

1. BMI≤15 kg/m². [Note: BMI=body mass index]
2. Abnormal kidney and liver function, defined as: serum creatinine 2.0 milligrams per deciliter (mg/dL).
3. An ongoing infection that requires systemic treatment, such as HIV, syphilis, or acute infectious disease. [Note: HIV=human immunodeficiency virus)]
4. Suffering from uncontrolled high blood pressure (SBP>180 mmHg, DBP>110 mmHg), diabetes (AC sugar>200 mg/dl).

5. Having uncontrolled diseases or medical history that the trial administrator considers to be ineligible for participation in this trial.

In this example, the method of Example 7 is used to obtain adipose-derived mesenchymal stem cells from the subject and expansion is performed. The steps are as follows.

Liposuction was performed from subjects during abdominal surgery. 2-5 g of adipose tissue was collected from the subcutaneous fat of the abdominal wall. The liposuction operation takes about 1 hour and the wound is less than 1 cm. All subjects provide informed consent form (ICF). Adipose tissue was placed in $Ca^{2+}/Mg^{2+}$-free phosphate buffered saline (PBS) and immediately transferred to the laboratory.

Human adipose tissue was removed from shipping medium and placed in a Petri dish. The adipose tissue was washed 3 to 4 times using $Ca^{2+}/Mg^{2+}$-free phosphate buffered saline (PBS) and cut into small pieces (volume approximately 1-3 mm$^3$). The tissue was dissociated with 0.1-0.3% collagenase in a temperature environment of 36.5-38.5° C. for 60 minutes. After collagenase digestion, centrifugation was performed at 20-25° C. and 500 g for 5-15 minutes to separate cells and undigested tissue fragments from stromal vascular fraction (SVF) pellets. The dissociated cells were collected and cultured at 36.5-38.5° C. in an incubator providing 5% $CO_2$. After 1 to 2 days of culture, the supernatant and debris were removed from the culture to obtain primary adipose-derived mesenchymal stem cells.

The primary adipose-derived mesenchymal stem cells were cultured in keratinocyte-serum free medium (SFM) (Gibco) comprising 1-100 mM N-acetyl-L-cysteine (Sigma) and 0.05-50 mM L-ascorbic acid 2-phosphate (Sigma)(the same culture medium components as in Example 1) in a culture flask made of a material with an oxygen-containing functional group at ratio of 20-35% (HYPERFlask, Corning) for 14 days. The number of cells is about 1.73-3.03×10$^8$. The culture environment is a cell culture incubator with a temperature controlled at 36.5-38.5° C. and containing 5% carbon dioxide.

The quality testing related to stem cells in this example is performed by a third-party certification laboratory. The sterility test is based on the Chinese Pharmacopoeia sterility test method and USP43, Sterility Tests, and is evaluated by the direct inoculation method. Gram stain is another rapid microbial detection test that uses staining to distinguish Gram positive/negative bacteria. *Mycoplasma* is evaluated using nucleic acid amplification technology based on the Chinese Pharmacopoeia *Mycoplasma* test method. Endotoxin testing is based on the Chinese Pharmacopoeia Bacterial Endotoxins Testing Method and USP43, Bacterial Endotoxins Tests, and is evaluated by kinetic colorimetry. Cell surface markers CD34, CD45, CD90, and CD105 (Becton Dickinson) were analyzed using a BD AccuriC6 flow cytometer (Becton Dickinson). Cell survival rate was assessed with ADAM-MC™ Automatic Cell Counter (Digital Bio, NanoEnTek Inc.).

The standards after adipose-derived mesenchymal stem cell expansion are shown in Table 9.

TABLE 9

| Indications | | Liver cirrhosis |
|---|---|---|
| Stem cell source | | Fat |
| Number of cells | | 1 × 10$^8$ ± 20% ADSCs |
| Cell activity (%) | | >70 |
| Cell surface antigen | CD34 | <10 |
| expression (%) | CD45 | <10 |

TABLE 9-continued

| | CD90 | >90 |
|---|---|---|
| | CD105 | >90 |
| | Safety | |
| Microbiological testing | | not detectable |
| Endotoxin testing (EU/mL) | | <0.25 |
| Mycoplasma test | | non-reactive |
| Excipients | | 1-1.2 mL of saline |
| Storage and resting conditions | | 2-10° C., 1-24 hours |
| Number of injections | | 1 or 2 |

Subject's basic information, abdominal adipose tissue sampling volume, cell number of adipose-derived mesenchymal stem cells before and after expansion, cell activity, cell surface antigen expression after expansion and safety of adipose-derived mesenchymal stem cells (aerobic and anaerobic bacteria, endotoxins, and *mycoplasma* content), and the results are recorded in Table 10.

TABLE 10

| Subject's basic information | |
|---|---|
| Characteristics\ Treatment | One injection |
| Age [Y] | |
| Min~Max | 41-65 |
| Body Weight [kg] | |
| Min~Max | 54.7-69.64 |
| Body Height [cm] | |
| Min-Max | 157.44-166.56 |
| Baseline BMI [kg/m$^2$] | |
| Min-Max | 19.95-24.89 |
| Gender | |
| Male | 75.0% |
| Female | 25.0% |
| Race | |
| Asian | 100.0% |
| Type liver cirrhosis | |
| alcoholic liver cirrhosis | 100% |
| Disease Duration [Y] | |
| Min-Max | 1.42-6.60 |
| Child-Pugh score | |
| Class A | 0.0% |
| Class B | 100.0% |
| Class C | 0.0% |
| Min-Max | 7-8 |
| MELD | |
| Min-Max | 11.80-13.48 |
| GOT | |
| Min-Max | 99-218 |
| GPT | |
| Min-Max | 35-85 |
| Total Bilirubin | |
| Min-Max | 1.92-3.48 |
| Albumin | |
| Min-Max | 3.21-4.53 |
| PT | |
| Min-Max | 12.39-15.27 |

TABLE 10-continued

Subject's basic information

| Characteristics\ Treatment | One injection |
|---|---|
| IL-10 | |
| Min-Max | 0.5-14.28 |
| INF-gamma | |
| Min-Max | 6.03-57.55 |
| Adipose tissue sampling amount (g) | |
| Min-Max | 3.90-4.84 |
| Before expansion Number of cells | |
| Min-Max | $9.78\text{-}24.6 \times 10^5$ |
| Cell activity (%) | |
| Min-Max | 71-87 |
| After expansion Number of cells | |
| Min-Max | $1.73\text{-}3.03 \times 10^8$ |

TABLE 10-continued

Subject's basic information

| Characteristics\ Treatment | | One injection |
|---|---|---|
| Cell activity (%) | | |
| Min-Max | | 95-97 |
| Cell surface antigen expression (%) | CD34 | 0.07-0.53 |
| | CD45 | 0.05-0.51 |
| | CD90 | 99.93-100.0 |
| | CD105 | 98.83-99.35 |
| Safety | | |
| Bacteria | | Not detected |
| Endotoxin | | <0.25 |
| Mycoplasma | | Non-reactive |

The adipose-derived mesenchymal stem cells expanded from the above-mentioned subjects were mixed with 1-1.2 ml of saline. The extracellular vesicles were stored and stood for 24 hours in an environment of 2-10° C. to obtain a composition comprising stem cells, extracellular vesicles and growth factors. Subjects underwent liver injection at week 0. Data were recorded 0, 1, 4, 8, 12, 16, 20 and 24 weeks after receiving the first treatment, as shown in Tables 11 and 12.

TABLE 11

Results of GOT, GPT, Child-Pugh score, MELD, bilirubin, albumin, PT, AFP, eGFR, creatinine, ammonia, IL-10, and INF-γ in subjects at 0, 1, 4, 8, 12, 16, 20, and 24 weeks after receiving first treatment

| NET CHANGE | 0 wk | 1 wk | 4 wk | 8 wk | 12 wk | 16 wk | 20 wk | 24 wk |
|---|---|---|---|---|---|---|---|---|
| GOT | 0 | −50.00 | −102.00 | −103.33 | −106.00 | −98.33 | −106.33 | −108.67 |
| GPT | 0 | 5.33 | −21.33 | −21.67 | −26.00 | −22.67 | −24.67 | −27.00 |
| Child-Pugh score | 0 | −1.33 | −1.67 | −1.67 | −1.67 | −1.67 | −2.33 | −2.33 |
| MELD | 0 | −1.97 | −3.34 | −3.11 | −3.94 | −3.54 | −3.84 | −3.46 |
| Bilirubin | 0.00 | −0.63 | −1.43 | −1.23 | −1.43 | −1.37 | −1.53 | −1.33 |
| Albumin | 0.00 | −0.03 | 0.00 | 0.07 | 0.10 | 0.23 | 0.20 | 0.10 |
| PT | 0.00 | −1.10 | −0.90 | −0.77 | −1.10 | −1.17 | −1.50 | −1.60 |
| AFP | 0.00 | −0.16 | 0.53 | −1.63 | −1.79 | −1.29 | −0.55 | −1.41 |
| eGFR | 0.00 | 10.33 | 16.00 | 11.00 | −3.00 | 10.67 | 3.33 | 8.33 |
| creatinine | 0.00 | −0.05 | −0.11 | −0.07 | −0.01 | −0.09 | −0.05 | −0.07 |
| ammonia | 0.00 | −2.00 | 11.33 | −5.67 | 8.33 | 29.67 | 10.00 | −15.33 |
| IL-10 | 0.00 | 0.23 | −1.01 | 5.87 | 7.98 | 9.19 | 5.30 | 6.97 |
| INF-gamma | 0.00 | 4.39 | 9.57 | 5.91 | 7.99 | 23.14 | 27.01 | 9.66 |

TABLE 12

The percentage of GOT, GPT, Child-Pugh score, MELD, bilirubin, albumin, PT, AFP, eGFR, creatinine, ammonia, IL-10, and INF-γ improvement in subjects at 0, 1, 4, 8, 12, 16, 20, and 24 weeks after receiving first treatment

| improved % | 0 wk | 1 wk | 4 wk | 8 wk | 12 wk | 16 wk | 20 wk | 24 wk |
|---|---|---|---|---|---|---|---|---|
| GOT | 0% | 37% | 64% | 65% | 66% | 61% | 66% | 68% |
| GPT | 0% | −7% | 31% | 33% | 42% | 35% | 42% | 46% |
| Child-Pugh score | 0% | 19% | 23% | 23% | 23% | 23% | 32% | 32% |
| MELD | 0% | 16% | 27% | 25% | 32% | 29% | 31% | 28% |
| Bilirubin | 0% | 29% | 52% | 42% | 49% | 46% | 55% | 41% |
| Albumin | 0% | −1% | 0% | 2% | 2% | 6% | 5% | 3% |
| PT | 0% | 7% | 6% | 5% | 7% | 7% | 10% | 11% |
| AFP | 0% | −4% | −19% | 11% | 15% | 9% | 1% | 11% |

TABLE 12-continued

The percentage of GOT, GPT, Child-Pugh score, MELD, bilirubin,
albumin, PT, AFP, eGFR, creatinine, ammonia, IL-10, and INF-γ
improvement in subjects at 0, 1, 4, 8, 12, 16, 20,
and 24 weeks after receiving first treatment

| improved % | 0 wk | 1 wk | 4 wk | 8 wk | 12 wk | 16 wk | 20 wk | 24 wk |
|---|---|---|---|---|---|---|---|---|
| eGFR | 0% | 10% | 17% | 13% | −1% | 13% | 6% | 10% |
| creatinine | 0% | 7% | 13% | 8% | −2% | 10% | 4% | 8% |
| ammonia | 0% | −4% | −19% | 11% | −8% | −49% | −13% | 27% |
| IL-10 | 0% | 2% | −7% | 1224% | 1388% | 1633% | 1004% | 846% |
| INF-γ | 0% | 133% | 142% | 182% | 183% | 440% | 385% | 196% |

The adipose-derived mesenchymal stem cells expanded from the above-mentioned subjects were mixed with 1-1.2 ml of saline. The extracellular vesicles were stored and stood for 24 hours in an environment of 2-10° C. to obtain a composition comprising stem cells, extracellular vesicles and growth factors. Subjects (Table 13) underwent liver injection at week 0 and week 24, respectively. Data were recorded 0, 1, 4, 18, 24, 25, 28, 32, 36, and 48 weeks after receiving the first treatment, as shown in Tables 14-17.

TABLE 13

Subject's basic information

| Characteristics\ Treatment | Two injection |
|---|---|
| Age [Y] | 60 |
| Body Weight [kg] | 68.5 |
| Body Height [cm] | 149.0 |
| Baseline BMI [kg/m$^2$] | 30.9 |
| Gender | |
| Male | 0.0% |
| Female | 100.0% |

TABLE 13-continued

Subject's basic information

| Characteristics\ Treatment | Two injection |
|---|---|
| Race | |
| Asian | 100.0% |
| Type liver cirrhosis | |
| alcoholic liver cirrhosis | 100% |
| Child-Pugh score | |
| Class A | 0.0% |
| Class B | 100.0% |
| Class C | 0.0% |
| Min~Max | 8 |
| MELD | 14.50 |
| GOT | 45 |
| GPT | 28 |
| Total Bilirubin | 2.9 |
| Direct Bilirubin | 1.4 |
| Albumin | 3 |
| PT | 13.1 |
| aPTT | 34.9 |
| INR | 1.25 |
| AFP | 5.5 |

TABLE 14

Results of GOT, GPT, total bilirubin, direct bilirubin,
albumin, PT, aPTT, INR, and AFP in subjects at
0, 1, 4, 18, 24, 25, 28, 32, 36, and 48 weeks
after receiving first treatment

| NET CHANGE | 0 wk | 1 wk | 4 wk | 18 wk | 24 wk | 25 wk | 28 wk | 32 wk | 36 wk | 48 wk |
|---|---|---|---|---|---|---|---|---|---|---|
| GOT | 0 | −6 | −1 | −7 | −12 | −16 | −11 | −11 | −14 | −20 |
| GPT | 0 | −5 | −4 | −8 | −9 | −10 | −7 | −9 | −11 | −12 |
| Total Bilirubin | 0 | 0.5 | −0.3 | −1.1 | −1.3 | −0.9 | −1.1 | −1.5 | −1.1 | −1.5 |
| Direct Bilirubin | 0 | 0.1 | −0.1 | −0.5 | −0.8 | −0.6 | −0.9 | −0.9 | −0.8 | −1 |
| Albumin | 0 | 0.1 | 0 | −0.1 | −0.1 | 0.1 | 0.2 | 0.4 | 0.3 | 0.6 |
| PT | 0 | −0.4 | −0.3 | −0.1 | −1.1 | −0.9 | −1.3 | −1.5 | −1.3 | −1.6 |
| aPTT | 0 | −1.7 | −4.1 | −1.8 | −2.9 | −2.7 | −3.6 | −3.3 | −3.5 | −5 |
| INR | 0 | 0.1 | −0.1 | −0.5 | −0.8 | −0.6 | −0.9 | −0.9 | −0.8 | −1 |
| AFP | 0 | 0.7 | −0.2 | −0.6 | −1.3 | −0.5 | −0.9 | 0.2 | −1.6 | −1 |

TABLE 15

The Child-Pugh score and MELD results of subjects at 0,
1, 24, 36 and 48 weeks after receiving first treatment

| NET CHANGE | 0 wk | 1 wk | 24 wk | 36 wk | 48 wk |
|---|---|---|---|---|---|
| Child-Pugh score | 0% | −1 | −2 | −2 | −3 |
| MELD | 0% | −1.5 | −4.8 | −4.6 | −5.8 |

TABLE 16

The percentage of GOT, GPT, total bilirubin, direct bilirubin,
albumin, PT, aPTT, INR, and AFP improvement in
subjects at 0, 1, 4, 18, 24, 25, 28, 32, 36, and 48
weeks after receiving second treatment

| improved % | 0 wk | 1 wk | 4 wk | 18 wk | 24 wk | 25 wk | 28 wk | 32 wk | 36 wk | 48 wk |
|---|---|---|---|---|---|---|---|---|---|---|
| GOT | 0% | 13% | 2% | 16% | 27% | 36% | 24% | 24% | 31% | 44% |
| GPT | 0% | 18% | 14% | 29% | 32% | 36% | 25% | 32% | 39% | 43% |
| Total Bilirubin | 0% | −17% | 10% | 38% | 45% | 31% | 38% | 52% | 38% | 52% |
| Direct Bilirubin | 0% | −7% | 7% | 1% | 9% | 7% | 10% | 12% | 10% | 12% |
| Albumin | 0% | 3% | 0% | −3% | −3% | 3% | 7% | 13% | 10% | 20% |
| PT | 0% | 3% | 2% | 1% | 8% | 7% | 10% | 11% | 10% | 12% |
| aPTT | 0% | 5% | 12% | 5% | 8% | 8% | 10% | 9% | 10% | 14% |
| INR | 0% | 3% | 2% | 1% | 9% | 7% | 10% | 12% | 10% | 12% |
| AFP | 0% | −13% | 4% | 11% | 24% | 9% | 16% | −4% | 29% | 18% |

TABLE 17

The percentage of improvement in Child-Pugh
score and MELD of subjects at 0, 1, 24, 36
and 48 weeks after receiving second treatment

| NET CHANGE | 0 wk | 1 wk | 24 wk | 36 wk | 48 wk |
|---|---|---|---|---|---|
| Child-Pugh score | 0% | 13% | 25% | 25% | 38% |
| MELD | 0% | 10% | 33% | 32% | 40% |

The liver is the organ richest in enzymes in the body. Aspartate aminotransferase (AST), also known as glutamic-oxalacetic transaminase (GOT), alanine aminotransferase (ALT), also known as glutamic pyruvic transaminase (GPT), albumin, prothrombin time and total bilirubin are all biochemical indices commonly used to evaluate liver function.

GOT and GPT mainly exist in liver cells. If liver cells are damaged by drugs, alcohol or viruses, GOT and GPT would be released from the liver cells into the blood, causing an exponential increase in the levels of GOT and GPT in the blood. Therefore, one of the indicators of liver function can be evaluated by measuring the levels of GOT and GPT in the blood. The general testing standards are that GOT should be less than 37U/L for men and less than 31U/L for women; GPT should be less than 41U/L for men and less than 31U/L for women.

Bilirubin in the blood is divided into direct bilirubin and indirect bilirubin, collectively called total bilirubin. Bilirubin is a product of the destruction of red blood cells and is absorbed and metabolized by the liver. When the liver's ability to metabolize bilirubin decreases, bilirubin flows into the bloodstream. Therefore, the total bilirubin content in the blood can be used as one of the indicators to evaluate the metabolic function of the liver. The normal range of total bilirubin is 0.3-1.0 μmol/l (mg/dl). The normal range of direct bilirubin is 0-0.2 μmol/l (mg/dl). Albumin is synthesized in liver cells, and its half-life is as long as 20 days. A significant decrease in the amount of albumin, thought to be caused by long-term inflammation or disease of the liver. Therefore, albumin is also used clinically as one of the indicators of liver function.

Albumin is produced by liver cells and has a half-life of 20 days. It is the most abundant protein in human plasma. Therefore, if the amount of albumin is significantly reduced, it may be caused by liver inflammation or disease. There-fore, albumin in blood can be used as one of the indicators to evaluate liver function. The normal range of albumin is 3.5-5.7 μmol/l (mg/dl).

Prothrombin is the precursor of coagulation factor. Various clotting factors are produced by the liver. Prothrombin time (PT)/activated partial thromboplastin time (aPTT) represents the time required for prothrombin to convert into thrombin to coagulate plasma. When the liver's production capacity decreases, clotting factors would decrease, resulting in prolonged clotting time. Therefore, PT or aPTT can be used as one of the indicators to evaluate liver function. The PT measured based on instruments and reagents of different brands are not necessarily the same, causing problems in data interpretation. Therefore, the INR value can reduce the differences between laboratories due to different methods and reagents. [INR=patient's measurement result/average result of normal people (ISI)]. The normal range of PT is 25.6-32.6 sec. The normal range of aPTT is 25.6-32.6 sec. The normal range of INR is 0.9-1.1 sec.

α-fetoprotein (AFP) is often used to screen for liver cancer. In addition, AFP expressions may also be seen during liver inflammation or during recovery. The normal range of AFP is 0-9 ng/ml.

Detecting the concentration of ammonia in the blood can be used to diagnose hepatic encephalopathy and hepatic coma caused by end-stage cirrhosis, liver failure, acute and subacute necrosis, and Reye's syndrome. Ammonia is metabolized by the liver. However, when liver cells are necrotic or damaged and cannot metabolize the protein product ammonia, it would be excreted from the gastrointestinal tract. Ammonia accumulation in the body causes brain lesions. The normal range of ammonia is 16-53 μmol/l.

Liver cirrhosis can be diagnosed by pathological sections, ultrasound, clinical symptoms and manifestations. The severity can be assessed from the following two classification methods.

(1) Child-Pugh score: In 1973, Pugh used a comprehensive scoring method to evaluate liver function based on the Child-Turcotte classification, and proposed the standard of Child-Pugh score, so that the original independent indicators can be fully considered, and they would not be overly affected by one indicator. The scores of these five items are added up and divided into three levels: A, B, and C. Level A is 5 to 6 points; Level B is 7 to 9 points; Level C is 10 to 15 points. C is the most serious (see Table 18).

TABLE 18

| Indicator score | 1 point | 2 points | 3 points |
|---|---|---|---|
| Hepatoencephalopathy | non | Mild | Moderate or severe |
| ascites | No ascites | Easy to control | Serious |
| Serum bilirubin (mg/dl) | <2 | 2-3 | >3 |
| Prothrombin time (seconds) | <4 | 4-6 | >6 |
| Albumin (g/dL) | >3.5 | 2.8-3.5 | <2.8 |

(2) Model for end stage liver disease (MELD) score:

In European and American countries, MELD score is used as an evaluation tool for liver transplantation. Items include total bilirubin, coagulation time, and renal function. The formula is calculated as follows.

MELD=3.78×ln[Serum bilirubin (mg/dL)]+11.2×ln [INR]+9.57×ln[Serum creatinine (mg/dL)]+6.43.

MELD score is used to evaluate the 3-month mortality of patients with liver cirrhosis over 12 years old.

The composition of the present invention is a suspension comprising at least stem cells, active synergistic ingredients, and growth factors, in which CD73 can be can highly expressed on stem cells. The results of the first treatment are shown in Tables 12-13, and the results of the second treatment are shown in Tables 15-17. After the first treatment, the composition of the present invention produces anti-inflammatory and anti-fibrosis effects by increasing IL-10 and INF-γ. The composition further reduces GOT and GPT, repairs liver damage or improves the regeneration ability of damaged liver, also enhances synthesis ability of albumin, metabolism ability of bilirubin, synthesis ability of prothrombin (such as PT, aPTT, and INR), and synthesis and metabolism ability of liver. Finally, Child-Pugh score and MELD are improved by 32% and 28% at 24 weeks. There are similar results in the second treatment, with final Child-Pugh score and MELD improved by 38% and 40%.

In summary, the composition comprising the mesenchymal stem cell (MSC), the extracellular vesicle (EV) produced by the mesenchymal stem cell, and the growth factor of the present invention has the following effect. Via liver injection, a suspension comprises at least stem cells, active synergistic ingredients, and growth factors, in which CD73 can be can highly expressed on stem cells, and the pharmaceutical composition can reduce aspartate aminotransferase (AST or GOT) and alanine aminotransferase (ALT or GPT) by highly expressing IL-10 and INF-γ. The pharmaceutical composition repairs liver damage and improves regeneration ability of damaged liver, and also enhances synthesis ability of albumin, metabolism ability of bilirubin, synthesis ability of prothrombin, and synthesis and metabolism ability of liver for more than half a year.

Although the present invention has been described with reference to the preferred embodiments, it will be apparent to those skilled in the art that a variety of modifications and changes in form and detail may be made without departing from the scope of the present invention defined by the appended claims.

What is claimed is:

1. A method for treating liver cirrhosis, comprising administering to a subject in need thereof a medicament comprising an effective amount of a composition comprising a mesenchymal stem cell (MSC), an extracellular vesicle (EV) produced by the mesenchymal stem cell, and a growth factor, wherein the growth factor is uteroglobin.

2. The method according to claim 1, wherein the mesenchymal stem cell is human adipose-derived mesenchymal stem cell (ADSC).

3. The method according to claim 1, wherein the liver cirrhosis is caused by alcoholic liver disease.

4. The method according to claim 1, wherein the growth factor is selected from the group consisting of: granulocyte colony-stimulating factor (G-CSF), granulocyte-macrophage colony-stimulating factor (GM-CSP), hepatocyte growth factor (HGF), insulin-like growth factor binding proteins-4 (IGFBP-4), insulin-like growth factor binding proteins-6 (IGFBP-6), interleukin-2 (IL-2), platelet-derived growth factor-AB/BB (PDGF-AB/BB), transforming growth factor-a (TGFa), vascular endothelial growth factor (VEGF-A), IL-18 binding protein-a (IL-18BPa), angiopoietin-like 3 (ANGPTL-3), fibroblast growth factor-19 (FGF-19), matrix metalloproteinase-2 (MMP-2), MMP-3, MMP-7, MMP-9, MMP-10, MMP-12, and a combination thereof.

5. The method according to claim 4, wherein the growth factor is IL-2, PDGF-AB/BB or TGFa, and expressions of the IL-2, PDGF-AB/BB and the TGFa are downregulated.

6. The method according to claim 1, wherein the mesenchymal stem cell has an effective concentration of liver injection of 7×107-1×108 mesenchymal stem cells.

7. The method according to claim 1, wherein the composition increases expressions of interleukin-10 (IL-10) and interferon gamma (INF-γ).

8. The method according to claim 1, wherein the composition reduces levels of aspartate aminotransferase (AST) and alanine aminotransferase (ALT).

9. The method according to claim 1, wherein the composition has ability to repair liver damage and improves regeneration ability of damaged liver.

10. The method according to claim 1, wherein the composition enhances synthesis ability of albumin, metabolism ability of bilirubin, synthesis ability of prothrombin, and synthesis and metabolism ability of liver.

11. The method according to claim 2, wherein the human ADSC is expanded by using the keratinocyte serum-free medium (SFM) supplemented with 1-100 mM N-acetyl-L-cysteine and 0.05-50 mM L-ascorbic acid 2-phosphate.

12. The method according to claim 11, wherein the human ADSC is further expanded in a culture flask made of a material with an oxygen-containing functional group at ratio of 20-35%.

13. The method according to claim 1, wherein therapeutic effect of the liver cirrhosis lasts for at least 6 months.

14. The method according to claim 1, wherein the medicament is in a dosage form for parenteral administration.

15. A medicament for treating liver cirrhosis, comprising a mesenchymal stem cell (MSC), an extracellular vesicle (EV) produced by the mesenchymal stem cell, and a growth factor, wherein the growth factor is uteroglobin.

* * * * *